United States Patent [19]

Terao et al.

[11] Patent Number: 5,290,679
[45] Date of Patent: Mar. 1, 1994

[54] METHOD OF PREDICTING THREATENED PREMATURE DELIVERY IN A PREGNANT WOMAN

[75] Inventors: Toshihiko Terao, Nagoya; Naohiro Kanayama, Hamamatsu; Akihiro Morioka, Nagoya; Yoshika Yasuda, Nagoya; Masami Kamiya, Nagoya; Juichi Awaya, Nagoya; Masayasu Kurono, Nagoya; Kiichi Sawai, Nagoya, all of Japan

[73] Assignee: Sanwa Kagaku Kenkyusho Co., Ltd., Nagoya, Japan

[21] Appl. No.: 898,681

[22] Filed: Jun. 15, 1992

[30] Foreign Application Priority Data

Jun. 18, 1991 [JP] Japan .................. 3-146221

[51] Int. Cl.$^5$ .................. C12Q 1/00; C12Q 1/37
[52] U.S. Cl. .................. 435/7.4; 435/23; 435/24
[58] Field of Search .................. 436/23, 24, 7.4

[56] References Cited

U.S. PATENT DOCUMENTS 4,458,013 7/1984 Ooyama .................. 435/7.4

FOREIGN PATENT DOCUMENTS

3016575A1 11/1981 Fed. Rep. of Germany .

OTHER PUBLICATIONS

Fischbach et al–Geburtshilfe Frauenheilkd (Jul. 1988) vol. 48, No. 7 pp. 469–478 (abst. supplied).
Kanayama et al–Nippon Sanka Fujinka Gakkai Zasshi--vol. 40 No. 7 pp. 917–918 (abst. supplied).
Kleesiek et al–Chem. Abst. vol. 105 (1986) 207139j.
Journal of Immunological Methods, vol. 131, 1990, pp. 41–48.
The Scandinavian Journal of Clinical and Laboratory Investigation, vol. 43, No. 5, Sep. 1983, pp. 427–432.
European Journal of Obstetrics & Gynecology and Reproductive Biology, vol. 34, No. 3, Mar. 1990, pp. 217–222.
Biological Abstracts, vol. 82, No. 10, (1986), Philadelphia, Pa., USA, p. 1036, abstract No. 97669.

*Primary Examiner*—Sam Rosen
*Attorney, Agent, or Firm*—Armstrong, Westerman, Hattori, McLeland & Naughton

[57] ABSTRACT

Even when the specimen contains human granulocyte elastase in the form of a mixture of free elastase with an elastase-inhibitor complex or complexes, the present invention enables the total quantity of elastase in that specimen to be precisely detected. The inhibitor is added to free elastase to convert it into an elastase-inhibitor complex, whereby the quantity of elastase can be measured by immunoassay as the total amount including the previously existing elastase-inhibitor complex. It is possible to precisely measure the total amount of elastase in mucus collected from the cervical canal of a pregnant woman, sputum or a rinsed solution of bronchovesicular lavage in which free elastase is mixed with an elastase-inhibitor complex. It is thus possible to predict and prevent threatened premature delivery, premature delivery or premature rupture of membranes by immunoassay of mucus collected from the cervical canal of a pregnant woman, to make a diagnosis of chronic or repetitive airway infections and pulmonary emphysema based on chronic respiratory diseases by immunoassay of sputum and a rinsed solution of bronchovesicular lavage and to make a diagnosis of urinary tract infections by immunoassay of urine.

1 Claim, 5 Drawing Sheets

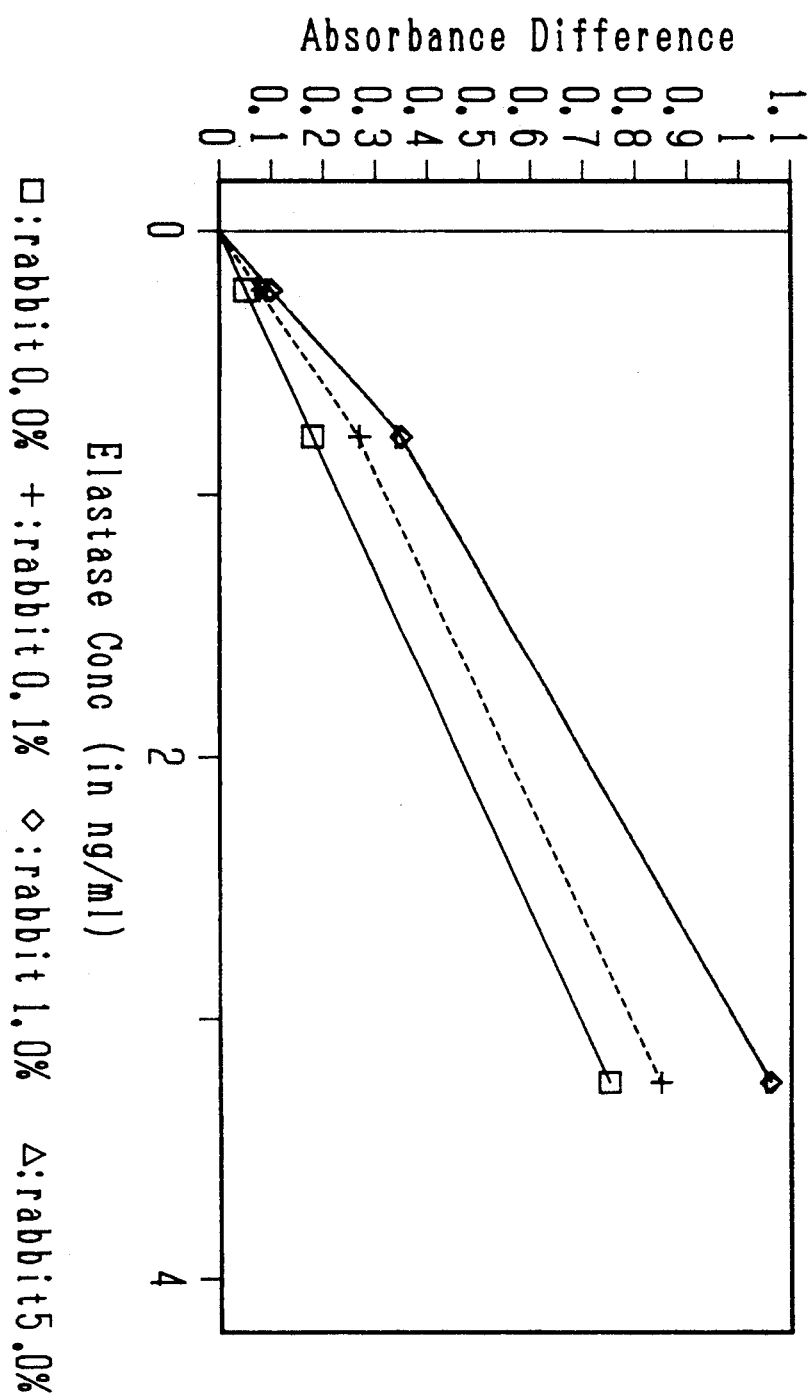

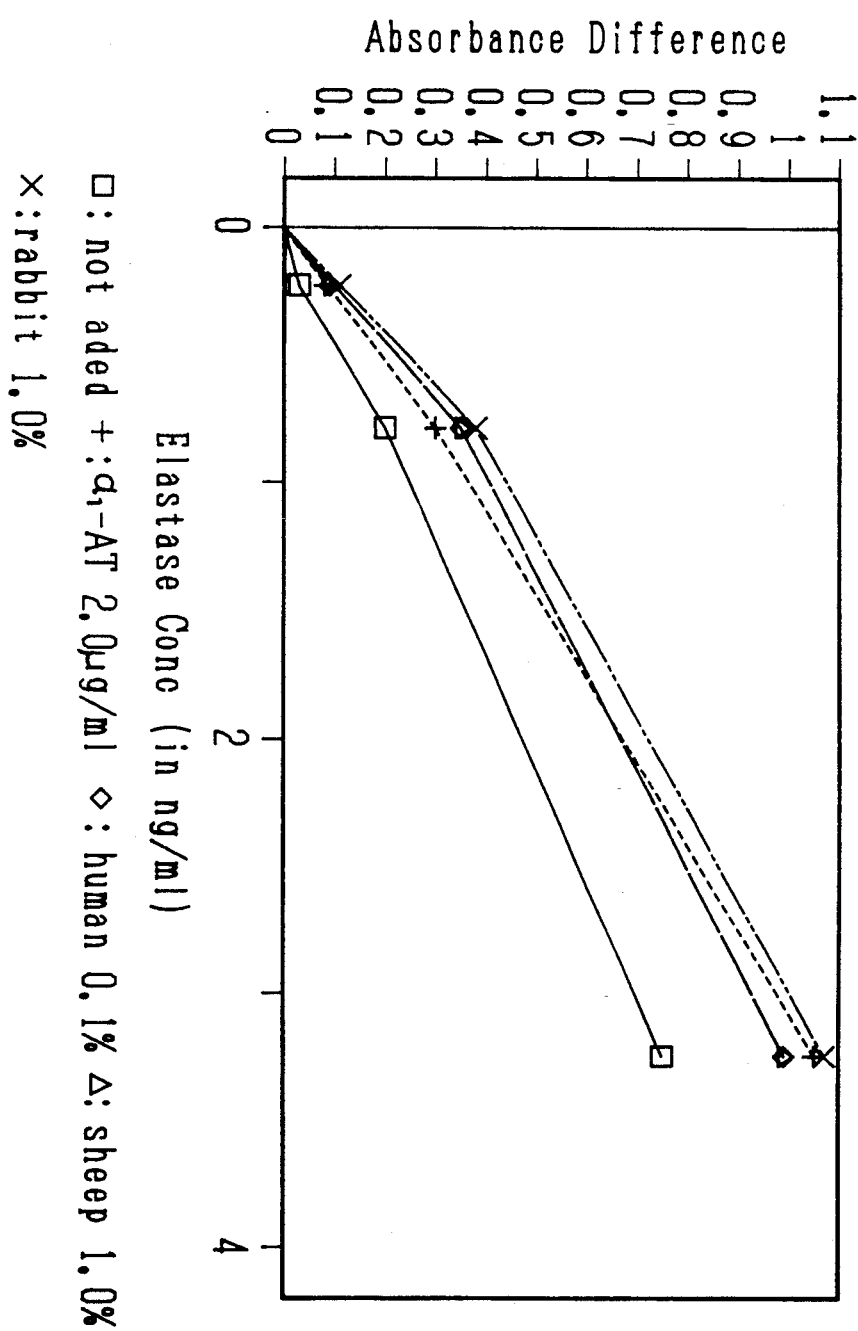

METHOD OF PREDICTING THREATENED PREMATURE DELIVERY IN A PREGNANT WOMAN

BACKGROUND OF THE INVENTION

1. Field of the Invention

The present invention relates generally to making immunoassay of human granulocyte elastase and, more particularly, to a method for precisely assaying the amount of human granulocyte elastase in the specimen to be assayed as the total amount of human granulocyte elastase, when that specimen contains a mixture of free elastase with an elastase-inhibitor complex as well as how to use it clinically.

2. Statement of the Prior Art

Human granulocytes are located in the forefront of the biophylaxis mechanism, gathering on the site of infection at the very initial stage of invasion and releasing proteases and active enzymes for decomposition, degradation and sterilization of foreign matters and bacteria. Of the released proteases, elastase has the strongest action and so holds a central position of the biophylaxis mechanism. However, on the other hand, this enzyme is too low in substrate specificity to decompose various connective tissue components (elastin, collagen, proteoglycan, etc.), inducing destruction of the living body's tissue due to digestion and degradation of constructive proteins.

Usually, a living body has in its blood a large amount of inhibitors, like $\alpha_1$-antitrypsin, so as to protect the tissue not subject to invasion against the strong digestive actions of enzymes; that is, even when elastase released from granulocytes gathering on the site of invasion is diffused throughout the living body by blood circulation, elastase-inhibitor complexes are immediately formed, whereby the activity of elastase is deactivated to prevent the tissue from being destructed more than required.

The determination of human granulocyte elastase playing such a role is considered very effective for diagnosis of inflammation or to clear up the cause of inflammation, treat it and judge recuperation, and a method of making imminoassay of the quantity of granulocyte elastase in blood is set forth in JP-A-57-551. According to this method, a elastase-inhibitor complex is immunologically assayed, using the first antibody an antibody for human granulocyte elastase and as the second antibody an enzyme labeled antibody for an inhibitor.

However, this method is used only for measuring elastase-inhibitor complexes; in other words, it lends itself fit for where circulating blood which contains the released human granulocyte elastase only in the form of an elastase-inhibitor complex is used as the specimen to be assayed. That is, a serious problem with this method is that when immunologically assaying specimens comprising tissular mucus obtained from the site of inflammation, which contains small amounts of inhibitors and in which free elastase is mixed with elastase-inhibitor complexes, the quantity of human granulocyte elastase cannot precisely be detected.

This is also true of when immunoassay is made using as the first antibody an antibody for human granulocyte elastase and as the second antibody an enzyme labeled antibody an inhibitor. In other words, the precise quantity of human granulocyte elastase cannot be detected, because there is a difference in the reactivities of said antibodies with free elastase and elastase-inhibitor complexes.

In view of the state-of-the-art problems mentioned above, the inventors have intensively studied of how to assay the precise quantity of human granulocyte elastase, even when free elastase is mixed with elastase-inhibitor complexes, and have accomplished the present invention.

SUMMARY OF THE INVENTION

According to this invention, the state-of-the-art problems mentioned above can be solved by the provision of a method of making immunoassay of human granulocyte elastase in a specimen, using an antibody for the human granulocyte elastase bonded to insoluble carriers, characterized in that when said enzyme is present in the form of a mixture of free elastase with elastase complexed with inhibitors present in the specimen to be assayed—hereinafter referred to an elastase-inhibitor complex or complexes, said free elastase is converted into an elastase-inhibitor complex by addition of an inhibitor capable of combining with said free elastase, and the thus converted elastase-inhibitor complex and the previously existing elastase-inhibitor complex are simultaneously assayed, thereby determining the total amount of human granulocyte elastase.

Preferably, the inhibitors which can combine with free elastase and so can be used in this invention are human $\alpha_1$-antitrypsin, human serum or plasma containing human $\alpha_1$-antitrypsin, animal serum or plasma containing a substance which can combine with free elastase in such a way that human $\alpha_1$-antitrypsin combines therewith to inhibit elastase activity and a synthetic material containing a substance which can combine with free elastase in such a way that human $\alpha_1$-antitrypsin combines therewith to inhibit elastase activity.

According to this invention, even when the specimen to be assayed contains a mixture of free elastase with elastase-inhibitor complexes, it is possible to assay the precise quantity of elastase and so present clinicians with precise data for diagnosis.

For instance, when the specimen to be assayed is mucus obtained from the cervical canal of a woman with child, which contains small amounts of inhibitors and in which free elastase is mixed with elastase-inhibitor complexes, it is possible to predict and prevent threatened premature delivery, premature delivery or premature rupture of membranes (PROM) by detecting the quantity of the granulocyte elastase precisely. One cause of threatened premature delivery, premature delivery or PROM is villous amnionitis which is considered to be developed by ascendant extention of cervicitis. Thus, whether or not there is cervicitis can be detected using the quantity of elastase released from granulocytes as a parameter, enabling the infection or inflammation to be treated at the early stage and preventing ascendant extention of the inflammation.

Sputum or a rinsed solution of bronchovesicular lavage also provides specimens which contain small amounts of inhibitors and in which free elastase is mixed with elastase-inhibitor complexes. Again, the presence of chronic and repetitive airway infections or pulmonary emphysema based on chronic respiratory diseases ascribable to elastase can be detected by assaying the quantity of elastase in these specimens, enabling the patients to receive pertinent treatment.

BRIEF DESCRIPTION OF THE DRAWINGS

FIG. 4 is a graphic representation showing the reactivities with respect to a human granulocyte elastase antibody of elastase-inhibitor complexes obtained by addition of rabbit sera to free elastase, and FIG. 5 is a graphic representation showing the reactivities with respect to a human granulocyte elastase antibody of elastase-inhibitor complexes obtained by addition of $\alpha_1$-antitrypsin (2.0 $\mu$g/ml), human serum (0.1%), sheet serum (1.0%) and rabbit serum (1.0%) to free elastase.

EXAMPLES

The present invention will now be explained specifically but not exclusively with reference to the examples.

EXAMPLE 1

What effects are obtained by adding to free elastase a human serum containing $\alpha_1$-antitrypsin as well as sheep and rabbit sera containing a substance having an effect similar to that of human $\alpha_1$-antitrypsin was investigated.

Free elastase was diluted and regulated to 500 ng/ml (22.4 U/l as enzyme activity) with a phosphate buffer solution (hereinafter PBS for short) (10 mM, pH 7.4), which contained human, sheep and rabbit sera, each in an amount of 0.0, 0.05, 0.1, 0.2, 0.5 or 1.0%, thereby preparing the specimens to be assayed. The enzyme activity of each specimen was determined with a synthetic substrate TESTTEAM S-2484 (Dai-ichi Kagaku) (hereinafter simply called S-2484) which reacts specifically with granulocyte elastase (cf. "Scad. J. Clin. Lab. Invest.", 43, 427(1983)). To this end, a solution of 80 $\mu$l of the specimen in 640 $\mu$l of a tris-hydrochloric acid buffer (hereinafter simply called the tris-HCl buffer) (0.05M, pH 8.3) containing sodium chloride (0.4M) and bovine serum albumin (0.125%) (Boehringer Mannheim GmbH)—hereinafter BSA for short—was incubated at 37° C. for 5 minutes. After this, 80 $\mu$l of S-2484 (6 mM) were added for a 3-minute incubation at 37° C., and 160 $\mu$l of acetic acid (50%) were added to stop the reaction. Aside from the above specimens, there was provided a specimen blank to which 50% acetic acid was added prior to addition of S-2484 and which was not subjected to a 3-minute incubation at 37° C. The absorbances of these specimens were determined at 405 nm with a microplate reader Model 450 (Bio-Rad Laboratories).

Figure 1:
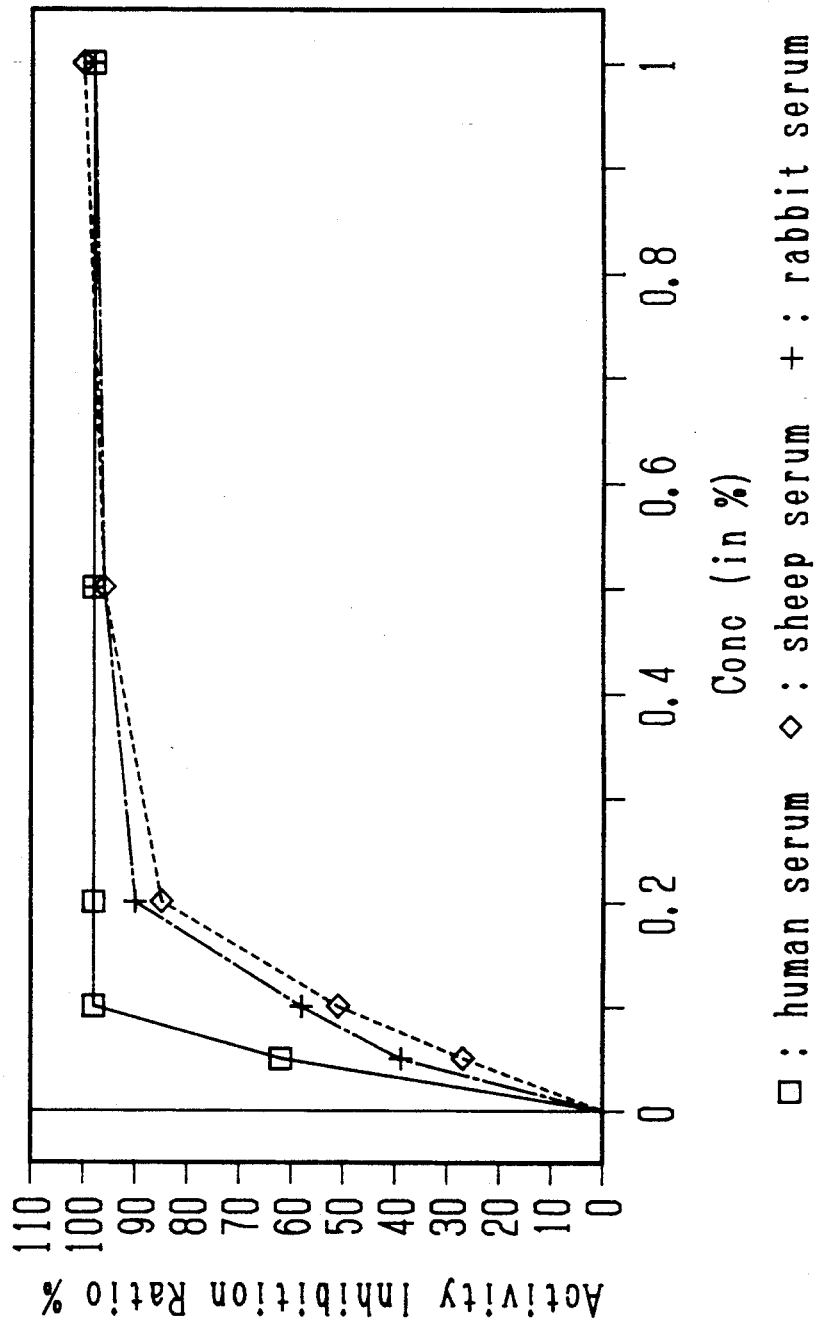
FIG. 1 is a graphic representation showing the inhibition ratios of various sera with respect to elastase activity.

Set out in Table 1 and FIG. 1 are the quantities of various sera added and the inhibition ratios of elastase activity, from which it has turned out that the sheep and rabbit sera act as an inhibitor for free elastase, as is the case with the human serum containing $\alpha_1$-antitrypsin, and forms an elastase-inhibitor complex, whereby the enzyme activity of elastase is inhibited. It has also turned out that the inhibition ratios of the enzyme activity increase depending upon the quantities of the sera and that the enzyme activity is almost completely inhibited when the amounts of the human serum and each of the sheep and rabbit sera added are 0.1% and 1.0%, respectively.

TABLE 1

Inhibition Ratios of Elastase Activity by Human, Sheep and Rabbit Sera Added

| Serum | Quantity (%) | Difference in Absorbance at 405 nm | Inhibition Ratio (%) |
|---|---|---|---|
| Human | 0.0 | 0.078 | 0.0 |
| | 0.05 | 0.029 | 62.8 |
| | 0.1 | 0.001 | 98.7 |
| | 0.2 | 0.001 | 98.7 |
| | 0.5 | 0.001 | 98.7 |
| | 1.0 | 0.002 | 97.4 |
| Sheep | 0.0 | 0.078 | 0.0 |
| | 0.05 | 0.048 | 38.5 |
| | 0.1 | 0.033 | 57.7 |
| | 0.2 | 0.008 | 89.7 |
| | 0.5 | 0.002 | 97.4 |
| | 1.0 | 0.002 | 97.4 |
| Rabbit | 0.0 | 0.078 | 0.0 |
| | 0.05 | 0.057 | 26.9 |
| | 0.1 | 0.038 | 51.3 |
| | 0.2 | 0.011 | 85.9 |
| | 0.5 | 0.002 | 97.4 |
| | 1.0 | 0.001 | 98.7 |

EXAMPLE 2

The reactivities of elastase-inhibitor complexes obtained by addition of human serum were investigated.

Free elastase was diluted and regulated to 0.0, 0.2, 0.8 and 3.2 ng/ml with PBSs containing 0.0, 0.01, 0.05, 0.01 and 0.2% of human sera, each including $\alpha_1$-antitrypsin as an inhibitor. Fifty (50) $\mu$l of each specimen were added to a microplate (Costar Corporation) coated by a sheep anti human granulocyte elastase antibody (Binding Site Ltd.). After a one-hour incubation at 37° C. the specimen was well washed with PBS containing polyoxyethylene (20) sorbitan monolaurate (0.05%) (Wako Junyaku), and was then added with 50 $\mu$l of a solution of peroxidase (POD)-labeled sheep anti human granulocyte elastase antibody (Binding Site Ltd.), followed by a one-hour incubation at 37° C. After this, the specimen was well washed with PBS containing polyoxyethylene (20) sorbitan monolaurate (0.05%). Added to this were 100 $\mu$l of a 0.1M citric acid/0.2M disodium hydrogenphosphate buffer solution—hereinafter called a McIrvein buffer solution—(pH 5.5), which contained o-phenylenediamine 2HCl (1 mg/ml, Wako Junyaku)—hereinafter OPD for short—and aqueous hydrogen peroxide (0.05%, Mitsubishi Gas), followed by a ten-minute reaction at room temperature. Then, 100 $\mu$l of 3N sulfuric acid (Wako Junyaku) were added to stop the reaction. To what degree the reaction solution developed colors was determined in terms of absorbance at 490 nm with a microplate reader (Model 450, Bio-Rad Laboratories).

Figure 2:
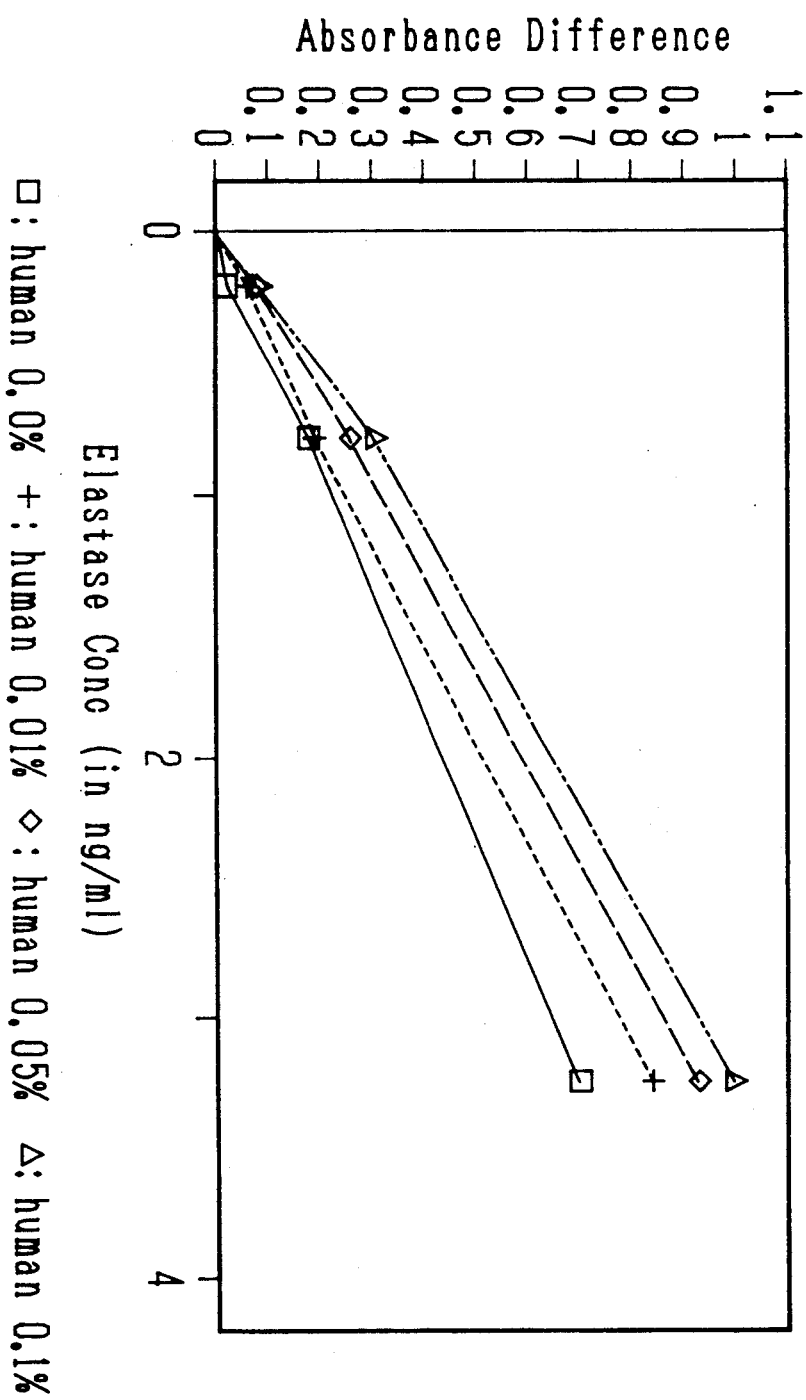
FIG. 2 is a graphic representation showing the reactivities with respect to a human granulocyte elastase antibody of elastase-inhibitor complexes obtained by addition of human sera to free elastase.

Set out and illustrated in Table 2 and FIG. 2 are the reactivities of the elastase-inhibitor complexes obtained by adding human serum to free elastase with respect to the human granulocyte elastase antibody in terms of absorbance changes. From these, it has turned out that in terms of the reactivity of the human granulocyte elastase antibody to the granulocyte elastase, the elastase-inhibitor complexes converted by addition of the human serum are better than free elastase. It has also turned out that the quantities of the elastase-inhibitor complexes converted increase depending upon the quantity of the human serum added, but the conversion to the elastase-inhibitor complexes are completed by addition of 0.1% of human serum.

TABLE 2

Reactivities of Elastase-Inhibitor Complexes Obtained by Addition of Human Serum

| Human Serum Quantity (%) | Elastase Conc. (ng/ml) | Absorbance 490 nm | Difference in Absorbance Δ490 nm |
|---|---|---|---|
| 0.0 | 0.0 | 0.119 | |
| | 0.2 | 0.156 | 0.037 |
| | 0.8 | 0.308 | 0.189 |
| | 3.2 | 0.834 | 0.715 |
| 0.01 | 0.0 | 0.123 | |
| | 0.2 | 0.183 | 0.060 |
| | 0.8 | 0.336 | 0.213 |
| | 3.2 | 0.968 | 0.845 |
| 0.05 | 0.0 | 0.163 | |
| | 0.2 | 0.234 | 0.071 |
| | 0.8 | 0.426 | 0.263 |
| | 3.2 | 1.114 | 0.951 |
| 0.1 | 0.0 | 0.211 | |
| | 0.2 | 0.284 | 0.073 |
| | 0.8 | 0.520 | 0.309 |
| | 3.2 | 1.210 | 0.999 |
| 0.2 | 0.0 | 0.306 | |
| | 0.2 | 0.387 | 0.081 |
| | 0.8 | 0.601 | 0.295 |
| | 3.2 | 1.308 | 1.002 |

EXAMPLE 3

The reactivities of elastase-inhibitor complexes obtained by addition of sheep serum were investigated.

Free elastase was diluted and regulated to 0.0, 0.2, 0.8 and 3.2 ng/ml with PBSs containing 0.0, 0.1, 1.0 and 5.0% of sheep sera. Fifty (50) μl of each specimen were added to a microplate coated by a sheep anti human granulocyte elastase antibody. After a one-hour incubation at 37° C. the specimen was well washed with PBS containing polyoxyethylene (20) sorbitan monolaurate (0.05%), and was then added with 50 μl of a solution of a peroxidase (POD)-labeled sheep anti human granulocyte elastase antibody, followed by a one-hour incubation at 37° C. After this, the specimen was well washed with PBS containing polyoxyethylene (20) sorbitan monolaurate (0.05%). Added to this were 100 μl of a McIrvein buffer solution containing OPD (1 mg/ml) and aqueous hydrogen peroxide (0.05%), followed by a ten-minute reaction at room temperature. Then, 100 μl of 3N sulfuric acid were added to stop the reaction. To what degree the reaction solution developed colors was determined in terms of absorbance at 490 nm with a microplate reader (Model 450, Bio-Rad Laboratories).

Figure 3:
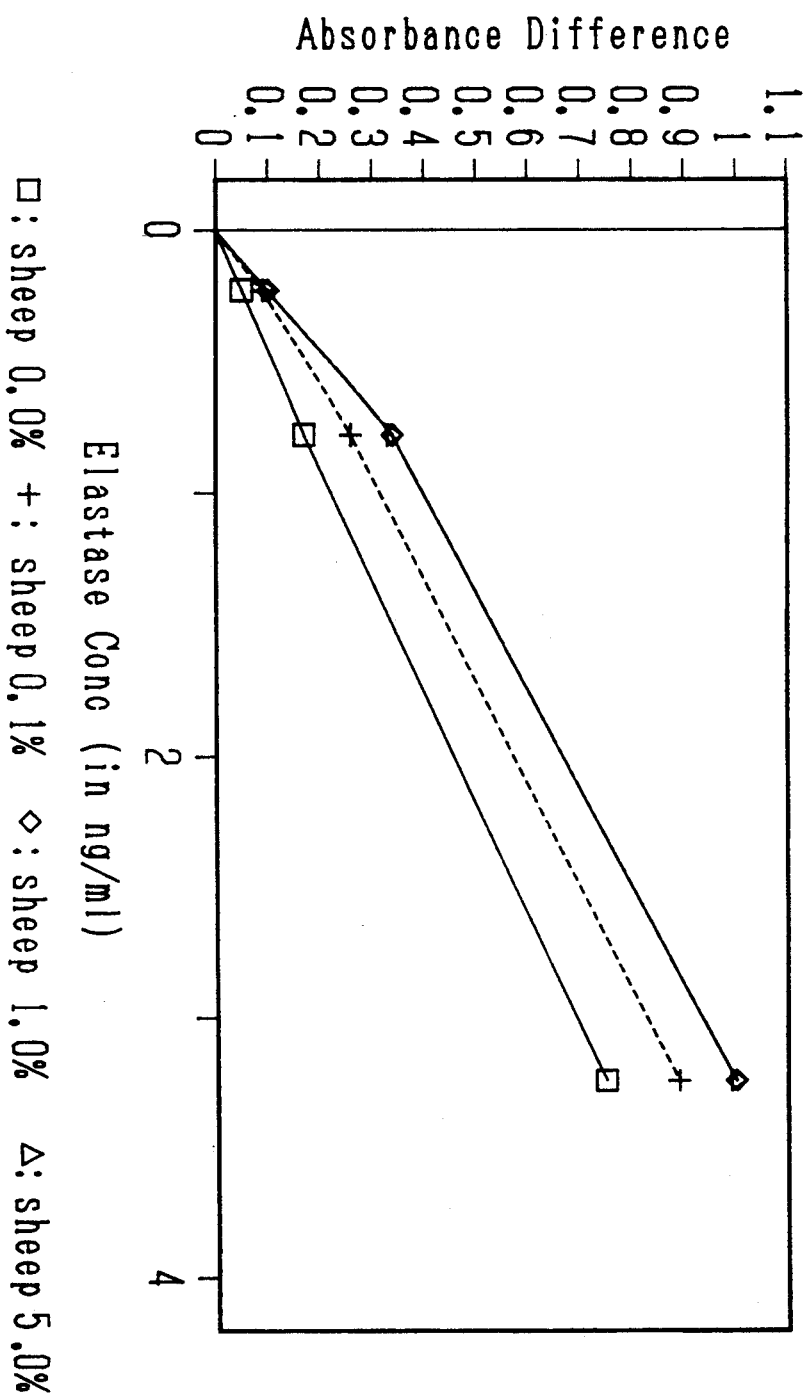
FIG. 3 is a graphic representation showing the reactivities with respect to a human granulocyte elastase antibody of elastase-inhibitor complexes obtained by addition of sheep sera to free elastase.

Set out and illustrated in Table 3 and FIG. 3 are the reactivities of the elastase-inhibitor complexes obtained by adding sheep serum to free elastase with respect to the human granulocyte elastase antibody in terms of absorbance changes. From these, it has turned out that in terms of the reactivity of the human granulocyte elastase antibody to the granulocyte elastase, the elastase-inhibitor complexes converted by addition of the sheep serum are better than free elastase. It has also turned out that the quantities of the elastase-inhibitor complexes converted increase depending upon the quantities of the sheep serum added, but the conversion to the elastase-inhibitor complexes is completed by addition of 1.0% of sheep serum.

TABLE 3

Reactivities of Elastase-Inhibitor Complexes Obtained by Addition of Sheep Serum

| Sheep Serum Quantity (%) | Elastase Conc. (ng/ml) | Absorbance 490 nm | Difference in Absorbance Δ490 nm |
|---|---|---|---|
| 0.0 | 0.0 | 0.162 | |
| | 0.2 | 0.210 | 0.048 |
| | 0.8 | 0.334 | 0.172 |
| | 3.2 | 0.889 | 0.727 |
| 0.1 | 0.0 | 0.144 | |
| | 0.2 | 0.213 | 0.069 |
| | 0.8 | 0.402 | 0.258 |
| | 3.2 | 1.033 | 0.889 |
| 1.0 | 0.0 | 0.157 | |
| | 0.2 | 0.244 | 0.087 |
| | 0.8 | 0.492 | 0.335 |
| | 3.2 | 1.158 | 1.001 |
| 5.0 | 0.0 | 0.158 | |
| | 0.2 | 0.246 | 0.088 |
| | 0.8 | 0.490 | 0.332 |
| | 3.2 | 1.156 | 0.998 |

EXAMPLE 4

The reactivities of elastase-inhibitor complexes obtained by addition of rabbit serum were investigated.

Free elastase was diluted and regulated to 0.0, 0.2, 0.8 and 3.2 ng/ml with PBSs containing 0.0, 0.1, 1.0 and 5.0% of rabbit sera. Fifty (50) μl of each specimen were added to a microplate coated by a rabbit anti human granulocyte elastase antibody. After a one-hour incubation at 37° C., the specimen was well washed with PBS containing polyoxyethylene (20) sorbitan monolaurate (0.05%), and was then added with 50 μl of a solution of a POD-labeled rabbit anti human granulocyte elastase antibody for a one-hour incubation at 37° C. After this, the specimen was well washed with PBS containing polyoxyethylene (20) sorbitan monolaurate (0.05%). Added to this were 100 μl of a McIrvein buffer solution containing OPD (1 mg/ml) and aqueous hydrogen peroxide (0.05%), followed by a ten-minute reaction at room temperature. Then, 100 μl of 3N sulfuric acid were added to stop the reaction. To what degree the reaction solution developed colors was determined in terms of absorbance at 490 nm with a microplate reader (Model 450, Bio-Rad Laboratories).

Set out and illustrated in Table 4 and FIG. 4 are the reactivities of the elastase-inhibitor complexes obtained by adding rabbit serum to free elastase with respect to the human granulocyte elastase antibody in terms of absorbance changes. From these, it has turned out that in terms of the reactivity of the human granulocyte elastase antibody to the granulocyte elastase, the elastase-inhibitor complexes converted by addition of the rabbit serum are better than free elastase. It has also turned out that the quantities of the elastase-inhibitor complexes converted increase depending upon the quantities of the rabbit serum added, but the conversion to the elastase-inhibitor complexes is completed by addition of 1.0% of rabbit serum.

TABLE 4

Reactivities of Elastase-Inhibitor Complexes Obtained by Addition of Rabbit Serum

| Rabbit Serum Quantity (%) | Elastase Conc. (ng/ml) | Absorbance 490 nm | Difference in Absorbance Δ490 nm |
|---|---|---|---|
| 0.0 | 0.0 | 0.162 | |
| | 0.2 | 0.210 | 0.048 |
| | 0.8 | 0.334 | 0.172 |

TABLE 4-continued

Reactivities of Elastase-Inhibitor Complexes
Obtained by Addition of Rabbit Serum

| Rabbit Serum Quantity (%) | Elastase Conc. (ng/ml) | Absorbance 490 nm | Difference in Absorbance Δ490 nm |
|---|---|---|---|
| | 3.2 | 0.889 | 0.727 |
| 0.1 | 0.0 | 0.141 | |
| | 0.2 | 0.207 | 0.066 |
| | 0.8 | 0.401 | 0.260 |
| | 3.2 | 0.985 | 0.844 |
| 1.0 | 0.0 | 0.136 | |
| | 0.2 | 0.233 | 0.097 |
| | 0.8 | 0.496 | 0.360 |
| | 3.2 | 1.198 | 1.062 |
| 5.0 | 0.0 | 0.138 | |
| | 0.2 | 0.235 | 0.097 |
| | 0.8 | 0.501 | 0.363 |
| | 3.2 | 1.205 | 1.067 |

EXAMPLE 5

Comparison between $\alpha_1$-antitrypsin, human serum, sheep serum and rabbit serum, all as inhibitors Free elastase was diluted and regulated to 0.0, 0.2, 0.8 and 3.2 ng/ml with PBSs, each containing $\alpha_1$-antitrypsin (2.0 μg/ml), human serum (0.1%), sheep serum (1.0%) and rabbit serum (1.0%) and PBS containing nothing. Fifty (50) μl of each specimen was added to a microplate coated by a rabbit anti human granulocyte elastase antiboty. After a one-hour incubation at 37° C., the specimen was well washed with PBS containing polyoxyethylene (20) sorbitan monolaurate (0.05%), and was then added with 50 μl of a solution of a POD-labeled rabbit anti human granulocyte elastase antiboty, followed by a one-hour incubation at 37° C. After this, the specimen was well washed with PBS containing polyoxyethylene (20) sorbitan monolaurate (0.05%). Added to this were 100 μl of a McIrvein buffer solution containing OPD (1 mg/ml) and aqueous hydrogen peroxide (0.05%) for a ten-minute reaction at room temperature. Then, 100 μl of 3N sulfuric acid were added to bring the reaction to an end. To what degree the reaction solution developed colors was determined in terms of absorbance at 490 nm with a microplate reader (Model 450, Bio-Rad Laboratories).

Set out and illustrated in Table 5 and FIG. 5 are the reactivities of the elastase-inhibitor complexes with respect to the human granulocyte elastase antibody in terms of absorbance changes, said complexes obtained by adding $\alpha_1$-antitrypsin (2.0 μg/ml), human serum (0.1%), sheep serum (1.0%) and rabbit serum (1.0%) to human elastase. It has turned out that the reactivities of the elastase-inhibitor complexes obtained by addition of various sera are substantially equivalent to that obtained by addition of 2.0 μg/ml of $\alpha_1$-antitrypsin, irrespective of the type of serum provided that it is added in the amount mentioned above.

TABLE 5

Comparison between $\alpha_1$-antitrypsin, human serum, sheep serum and rabbit serum, all as inhibitors

| Additive | Quantity | Elastase Conc. (ng/ml) | Absorbance 490 nm | Difference in Absorbance Δ490 nm |
|---|---|---|---|---|
| — | — | 0.0 | 0.119 | |
| | | 0.2 | 0.156 | 0.037 |
| | | 0.8 | 0.308 | 0.189 |
| | | 3.2 | 0.834 | 0.715 |
| $\alpha_1$-antitrypsin | 2.0 μg/ml | 0.0 | 0.123 | |
| | | 0.2 | 0.206 | 0.083 |
| | | 0.8 | 0.418 | 0.295 |
| | | 3.2 | 1.163 | 1.040 |
| Human serum | 0.1% | 0.0 | 0.211 | |
| | | 0.2 | 0.284 | 0.073 |
| | | 0.8 | 0.500 | 0.289 |
| | | 3.2 | 1.190 | 0.979 |
| Sheep serum | 1.0% | 0.0 | 0.157 | |
| | | 0.2 | 0.244 | 0.087 |
| | | 0.8 | 0.492 | 0.335 |
| | | 3.2 | 1.158 | 1.001 |
| Rabbit serum | 1.0% | 0.0 | 0.136 | |
| | | 0.2 | 0.233 | 0.097 |
| | | 0.8 | 0.496 | 0.360 |
| | | 3.2 | 1.198 | 1.062 |

EXAMPLE 6

Immunoassay of granulocyte elastase in mucous specimens obtained from the cervical canal of a woman with child Mucus was obtained from the cervical canal of a woman with child with a swab (Abbot Lab.), and this swab was immersed in PBS (1 ml). Then, the mucus was well stirred in PBS and centrifuged at 1000 rpm for 5 minutes to collect the supernatant fluid as the specimen to be assayed.

For immunoassay, the specimen was diluted 500-fold with PBS containing sheep serum (1.0%), and 50 ml were then added to a microplate coated by a sheep anti human granulocyte elastase antibody. At the same time, free elastase standard solutions (0.2, 0.4, 0.8, 1.6 and 3.2 ng/ml) were diluted with a similar diluent to prepare standard lines, and 50 μl of each solution were added to the same microplate to which the specimen was added. After a one-hour incubation at 37° C., each specimen was well washed with PBS containing polyoxyethylene (20) sorbitan monolaurate (0.05%), and was then added with 50 μl of a solution of a POD-labeled rabbit anti human granulocyte elastase antibody, followed by a one-hour incubation at 37° C. After this, the specimen was well washed with PBS containing polyoxyethylene (20) sorbitan monolaurate (0.05%). Added to this were 100 μl of a McIrvein buffer solution containing OPD (1 mg/ml) and aqueous hydrogen peroxide (0.05%) for a ten-minute reaction at room temperature. Then, 100 μl of 3N sulfuric acid were added to bring the reaction to an end. To what degree the reaction solution developed colors was determined in terms of absorbance at 490 nm with a microplate reader (Model 450, Bio-Rad Laboratories). The concentration of elastase in the specimen could be determined from the absorbances of the standard solutions and specimen. In consequence, it has turned out that the concentration (as measured in the extract) of granulocyte elastase in the mucus of the cervical canal of a woman with child kept sound until delivery is low, but that of a pregnant woman threateningly and prematurely delivered of a child is high. Thus, it is possible to predict threatened premature delivery by assaying the concentration of granulocyte elastase in the mucus of the cervical canal of a pregnant woman. Set out below are the results of this example.

TABLE 6

Mucous Specimens from the Cervical Canal
Concentration and Absorbance of Elastase Standard Solution

| Elastase Standard Solution Conc. (ng/ml) | Absorbance (490 nm) |
| --- | --- |
| 0.0 | 0.133 |
| 0.2 | 0.216 |
| 0.4 | 0.281 |
| 0.8 | 0.432 |
| 1.6 | 0.720 |
| 3.2 | 1.246 |

Results of Measurement of the Mucus of the Cervical Canal

| Specimen No. | Absorbance (490 nm) | Elastase Conc. (ng/ml) | Elastase Conc. in the Extract (μg/ml) | Clinical Conditions |
| --- | --- | --- | --- | --- |
| 1 | 0.612 | 1.31 | 0.66 | * |
| 2 | 0.190 | 0.15 | 0.08 | ** |
| 3 | 0.297 | 0.44 | 0.22 | ** |
| 4 | 0.722 | 1.61 | 0.81 | * |
| 5 | 0.238 | 0.27 | 0.14 | ** |

*: Threatened premature delivery observed.
**: Remained sound until delivery.

EXAMPLE 7

Immunoassay of granulocyte elastase in urine

Five (5) ml of urine were centrifuged at 1000 rpm for 5 minutes, and the supernatant fluid was pooled as the specimen to be assayed.

For immunoassay, the specimen was diluted to 500-folds with PBS containing sheep serum (1.0%), and 50 ml were then added to a microplate coated by a sheep anti human granulocyte elastase antibody. At the same time, free elastase standard solutions (0.2, 0.4, 0.8, 1.6 and 3.2 ng/ml) were diluted with a similar diluent to prepare standard lines, and 50 μl of each solution were added to the same microplate to which the specimen was added. After a one-hour incubation at 37° C., each specimen was well washed with PBS containing polyoxyethylene (20) sorbitan monolaurate (0.05%), and was then added with 50 μl of a solution of a POD-labeled rabbit anti human granulocyte elastase antibody, followed by a one-hour incubation at 37° C. After this, the specimen was well washed with PBS containing polyoxyethylene (20) sorbitan monolaurate (0.05%). Added to this were 100 μl of a McIrvein buffer solution containing OPD (1 mg/ml) and aqueous hydrogen peroxide (0.05%) for a ten-minute reaction at room temperature. Then, 100 μl of 3N sulfuric acid were added to bring the reaction to an end. To what degree the reaction solution developed colors was determined in terms of absorbance at 490 nm with a microplate reader (Model 450, Bio-Rad Laboratories). The concentration of elastase in the specimen could be determined from the absorbances of the standard solutions and specimen. In consequence, it has turned out that the concentration of granulocyte elastase in the urine of those who are healthy is low, but that of those who have urinary tract infections is high. It is thus possible to make a diagnosis of urinary tract infections by assaying the concentration of granulocyte elastase in urine. Set out in Table 7 are the results of this example.

TABLE 7

Urine Specimens
Concentration and Absorbance of Elastase Standard Solution

| Elastase Standard Solution Conc. (ng/ml) | Absorbance (490 nm) |
| --- | --- |
| 0.0 | 0.133 |
| 0.2 | 0.216 |
| 0.4 | 0.281 |
| 0.8 | 0.432 |
| 1.6 | 0.720 |
| 3.2 | 1.246 |

Results of Urine Measurement

| Specimen No. | Absorbance (490 nm) | Elastase Conc. (ng/ml) | Elastase Conc. in Urine (μg/ml) | Clinical Conditions |
| --- | --- | --- | --- | --- |
| 1 | 1.153 | 2.91 | 1.46 | * |
| 2 | 0.157 | 0.03 | 0.02 | ** |
| 3 | 0.188 | 0.12 | 0.06 | ** |
| 4 | 1.045 | 2.58 | 1.29 | * |
| 5 | 0.238 | 0.25 | 0.13 | ** |
| 6 | 0.101 | *** | *** | ** |

*: Urinary tract infections
**: Sound
***: Not detectable

What is claimed is:

1. An immunoassay method for predicting premature delivery in a pregnant woman which comprises a) obtaining mucus from the cervical canal of the pregnant woman, said mucus containing free granulocyte elastase and granulocyte elastase complexed with an inhibitor; b) adding an inhibitor to convert the free granulocyte elastase to inhibited granulocyte elastase; and c) measuring the total amount of granulocyte elastase complexed with an inhibitor contained in said mucus and the inhibited granulocyte elastase formed by addition of the inhibitor to the free elastase in said mucus, an elevated level of said total amount being indicative of threatened premature delivery.

* * * * *